United States Patent [19]

Druskoczi

[11] Patent Number: 5,010,877
[45] Date of Patent: Apr. 30, 1991

[54] SURGICAL COLLAR AND LINER THEREFOR

[76] Inventor: Sue Druskoczi, 64 Second St., Fairfield, Conn. 06430

[21] Appl. No.: 440,716

[22] Filed: Nov. 24, 1989

[51] Int. Cl.⁵ .......................... A61F 5/01; A61F 5/00
[52] U.S. Cl. ................................ 128/87 B; 128/87 R; 128/76 R; 128/DIG. 23; 2/143; 2/272; 2/DIG. 7
[58] Field of Search ............... 128/87 R, 87 B, 163, 128/DIG. 23, 76 R, 857; 2/129, 143, 243 B, 272, DIG. 7

[56] References Cited

U.S. PATENT DOCUMENTS

| | | | |
|---|---|---|---|
| 773,716 | 11/1904 | Crogin | 128/DIG. 23 |
| 1,473,506 | 11/1923 | Nessler | 128/DIG. 23 |
| 2,818,063 | 12/1957 | Smith et al. | 128/87 B |
| 2,911,970 | 11/1959 | Bartels | 128/DIG. 23 |
| 3,810,466 | 5/1974 | Rogers | 128/DIG. 23 |
| 3,921,626 | 11/1975 | Neel | 128/DIG. 23 |
| 4,572,173 | 2/1986 | Comeau | 128/857 |
| 4,712,540 | 12/1987 | Tucker | 128/76 R |
| 4,718,412 | 1/1988 | Nesbitt | 128/87 R |

Primary Examiner—Richard J. Apley
Assistant Examiner—Karen G. Horowitz
Attorney, Agent, or Firm—Arthur J. Fattibene; Paul A. Fattibene

[57] ABSTRACT

This disclosure is directed to a liner and a surgical collar wherein the liner is formed of a blank of soft, pliable absorbent material shaped to conform to the interior surface of the surgical collar and having opposed reversible folded pockets formed along the opposed ends of the blank for receiving the edges of the surgical collar and a reversible foldable edge flange for overlying the upper peripheral portion of the surgical collar so as to render the collar more comfortable to the wearer. The liner may be formed as a unitary member, or in several parts, depending upon the specific construction of the surgical collar.

7 Claims, 5 Drawing Sheets

SURGICAL COLLAR AND LINER THEREFOR

FIELD OF INVENTION

This invention is directed to a surgical collar and more specifically, to a liner for in combination with a surgical collar.

PROBLEM AND PRIOR ART

Surgical collars are frequently required to be worn by patients to maintain the head and/or neck immobile as a result of an accident, injury or surgical procedure. More often than not, such surgical collars are required to be worn continuously by the patient over a considerable period of time. Usually, such collars are formed of a relatively rigid body portion defining a brace which circumscribes the patient's neck, suitably shaped to confine the sides of the head and chin of the patient so as to maintain the head immobile relative to the neck. Such collars along the inner surface may be provided with a rubber or foam pad which are currently formed of a plastic foam-like material. Such plastic foam material has a surface which is generally non-porous and non-absorbent. As a result, the closeness of such foam or rubber-like liner against a patient's skin, and particularly in hot and humid weather, causes the skin to perspire, thus rendering the wearing of such collar extremely uncomfortable. Because of perspiration, such pads acquire an unpleasant gym smell and are difficult to clean and/or wash. Also, because of perspiration and the foam or rubberized nature of the collar padding, one's skin after prolonged wear can become irritated and cause a very discomforting rash.

OBJECTS

An object of this invention is to provide an absorbent liner for use with a surgical collar which can be rendered readily detachably connected and which is readily absorbent and easy to wash or clean.

Another object is to provide an absorbent liner so as to render the wearing of a surgical collar more comfortable to the patient.

Another object is to provide a surgical collar liner which is formed of a soft absorbent material which can be readily fitted to the shape of the surgical collar and secured in place thereon.

Another object is to provide a liner for a surgical collar which is readily simple in construction, can be economically fabricated and which is simple to use.

SUMMARY OF THE INVENTION

The foregoing objects and other features and advantages are attained by a surgical collar liner which is formed out of a blank of soft, absorbent material which is pre-formed and shaped so that it can be readily fitted to a standard surgical collar. In one form of the invention, the liner is formed so as to be attached to a unitary type of standard collar and which liner comprises a blank of material having reversely folded marginal end portions to define an end pocket for receiving the opposed ends of the unitary surgical collar. One of the end pockets is provided with a slit through which the fastening strap of the collar is extended. The upper longitudinal marginal portion of the blank is adapted to be reversely folded about the upper peripheral portion of the surgical collar to aid in maintaining the liner properly fitted to the collar. If desired, the lower longitudinal marginal portion of the blank may likewise be reversely folded about the bottom edge of the collar.

In another form of the invention, the liner may be made in two half sections, each being formed of a soft pliable, absorbent material having similar reversely folded end portions to define end pockets for receiving the opposed ends of a segmented surgical collar and having reversely folded longitudinal marginal flaps to secure the liner to its complimentary surgical collar section.

FEATURES

A feature of this invention resides in the provision of a liner which is constructed so as to be readily fitted to the interior surface of a surgical collar.

Another feature resides in the provision of a unitary liner having end pockets for receiving the opposed ends of a unitary surgical collar and having a slit formed at one end through which the fastening strap of the collar is extended.

Another feature resides in the provision of a liner formed in two half sections, each being fitted to a surgical collar which is formed in two sections.

Other features and advantages will become more readily apparent when considered in view of the drawings in which.

DETAIL DESCRIPTION

Figure 1:
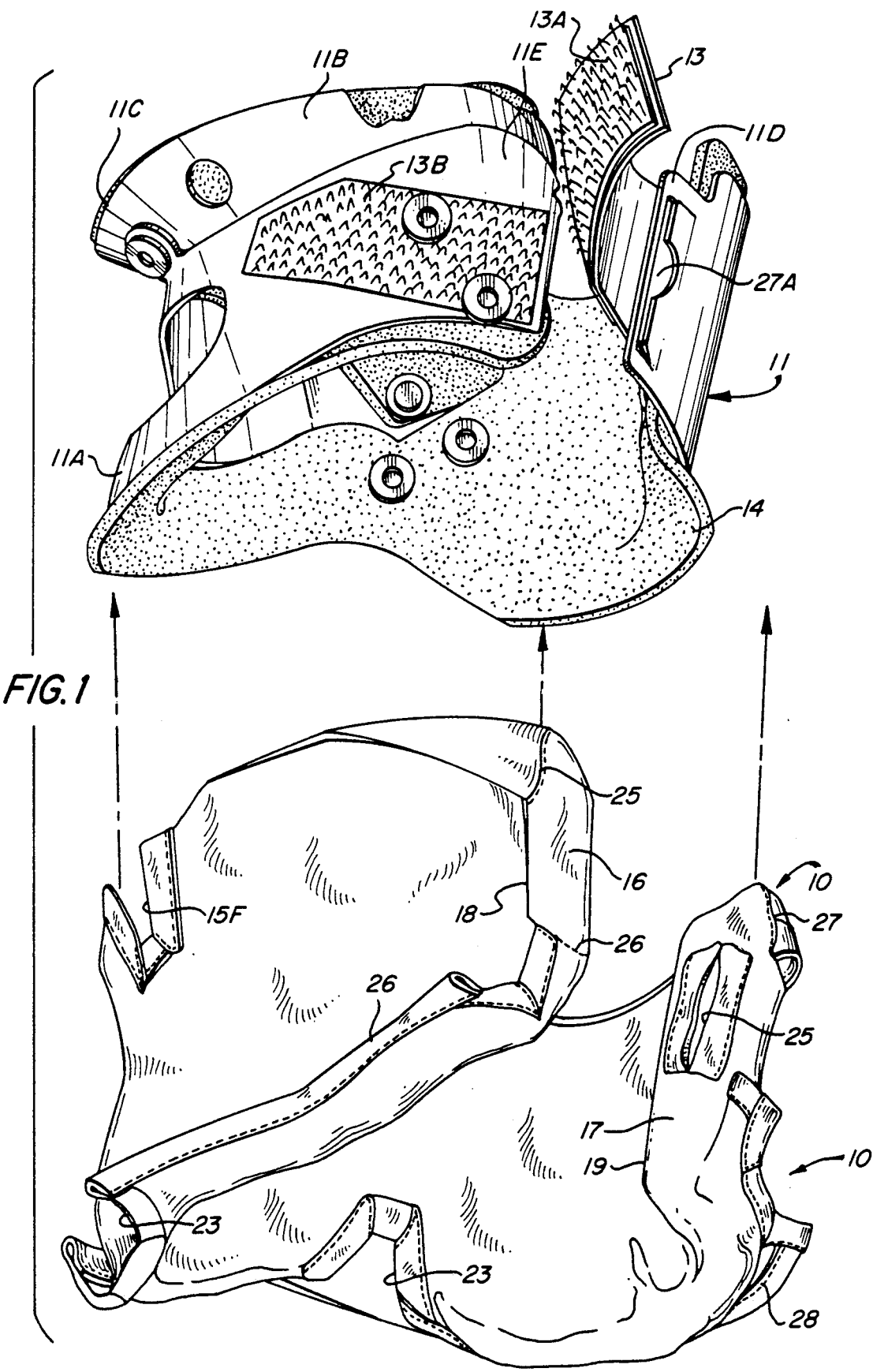
FIG. 1 is a perspective exploded view of a surgical collar and liner therefor embodying the invention.

Referring to FIG. 1, there is shown the liner 10 embodying the invention as applied to a surgical collar 11. The surgical collar 11 comprises a standard, readily available collar construction which consists of molded plastic member 11A which defines the body portion adapted to circumscribe the neck of the wearer. Connected to the upper end of the body portion 11A is an extended portion 11B which is shaped to define a chin rest 11C. Connected to one end 11D of the body portion 11A is a Velcro fastening strap 13. Attached to the other end 11E is a piece of complementary hook and loop material or hook type material 13B for receiving the looped portion 13A of the Velcro fastening strap 13. Connected along the inner surfaces of the respective body portion 11 and connected chin rest or extended portion 11B is a soft plastic foam pad 14.

Figure 5:
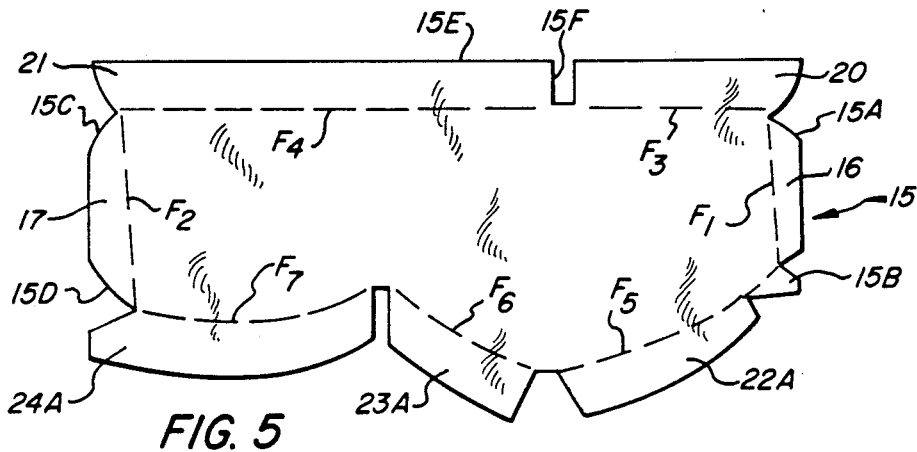
FIG. 5 is a detail plan view of the blank from which the liner of FIGS. 3 and 4 is formed.

In accordance with this invention, a liner 10 is provided so as to render the wearing of such surgical collar 11 more comfortable to the patient. The liner 10 is formed from a blank of soft, pliable sheet material which is readily absorbent, e.g., a terrycloth or towel-like fabric. As best seen in FIGS. 1 to 3-6, the liner 10 comprises a blank 15 which is constructed to conform to the inner surface of the collar 11. The blank 15 is cut to define a pattern generally of the outline shown in FIG. 5. As shown in FIG. 5, the pattern for the liner 10 is provided with side notches 15A, 15B, 15C and 15D at the opposed ends of the blank 15. Extending generally between notch 15A, 15B and 15C, 15D respectively is a foldline $F_1$ and $F_2$ to define a marginal end flap 16 and 17 which are adapted to be reversely folded about its respective folding $F_1$ and $F_2$ *l as will be hereinafter described to form end pockets* 18 *and* 19 *respectively.*

The upper edge 15E is provided with a notch 15F arranged so as to be located at the chin rest portion 11C of the collar, and which notch 15F in the assembled position of the liner 10 facilitates the liner to circumscribe the inner surface of the collar 11. Extending horizontally along the upper edge 15E and generally parallel thereto and extending between notches 15A and 15C is a foldline $F_3$, $F_4$ defining top marginal flaps 20, 21. The bottom edge is provided with a pair of notches 22, 23 to facilitate conforming the liner to the interior shape of the collar 11. Extending generally parallel to the bottom edge of the liner blank 15 are foldlines $F_5$, $F_6$ and $F_7$ to define bottom marginal flaps 22A, 23A and 24A.

Figure 3:
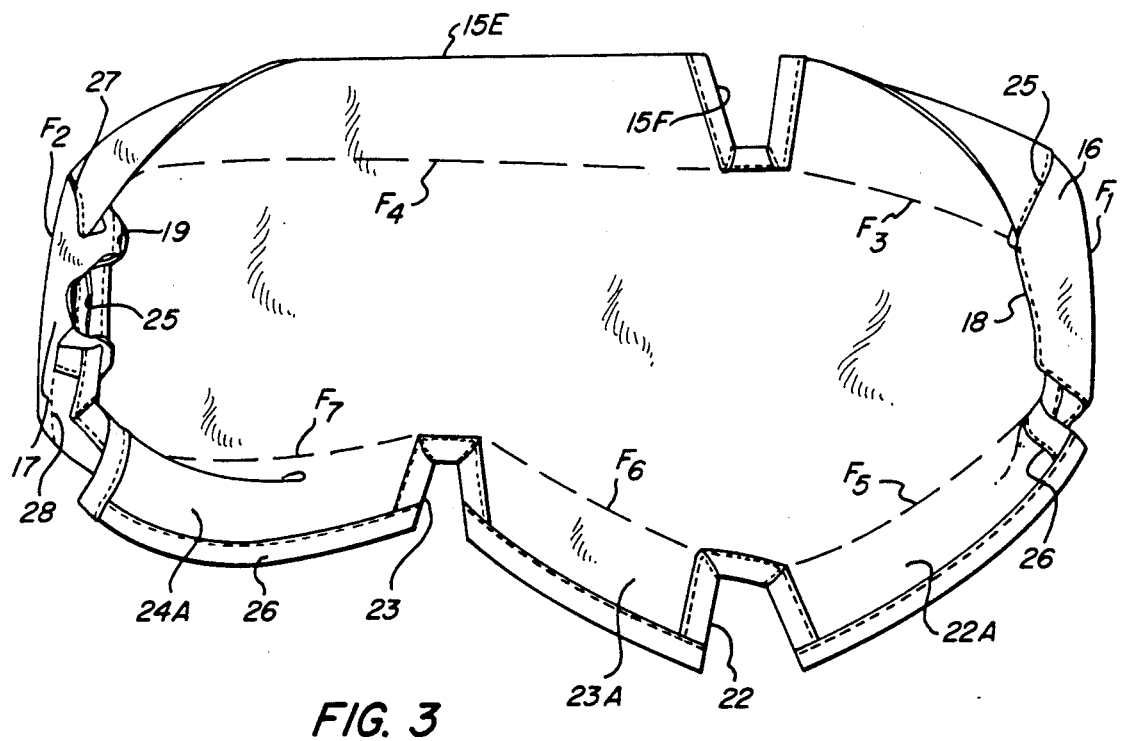
FIG. 3 is a plan view of the liner of FIG. 2 showing the outer side thereof which engages the inner surface of the surgical collar.

To assemble the liner blank 15 described to form the liner 10, the marginal end flap 16 and 17 are reversely folded as shown in FIG. 3 so that the continguous edges of the opposed notches 15A, 15B and 15C, 15D respectively can be readily secured to the end flap therebetween as by a sewn seam as indicated at 25, 26 and 27,28 respectively so that the adjacent edges of the upper and lower flaps are secured to the opposed ends of the end flaps 16 and 17. As shown in FIG. 3, end pockets 18 and 19 are formed at the opposed ends of the liner; which are arranged to receive the ends 11E and 11D of the collar 11. Adjacent to end pocket 19, the liner is provided with a slit 25. If desired, a binding or hem 26 may be formed along the peripheral portion of the liner blank 15, e.g., along the bottom and ends of the blank 15.

Figure 2:
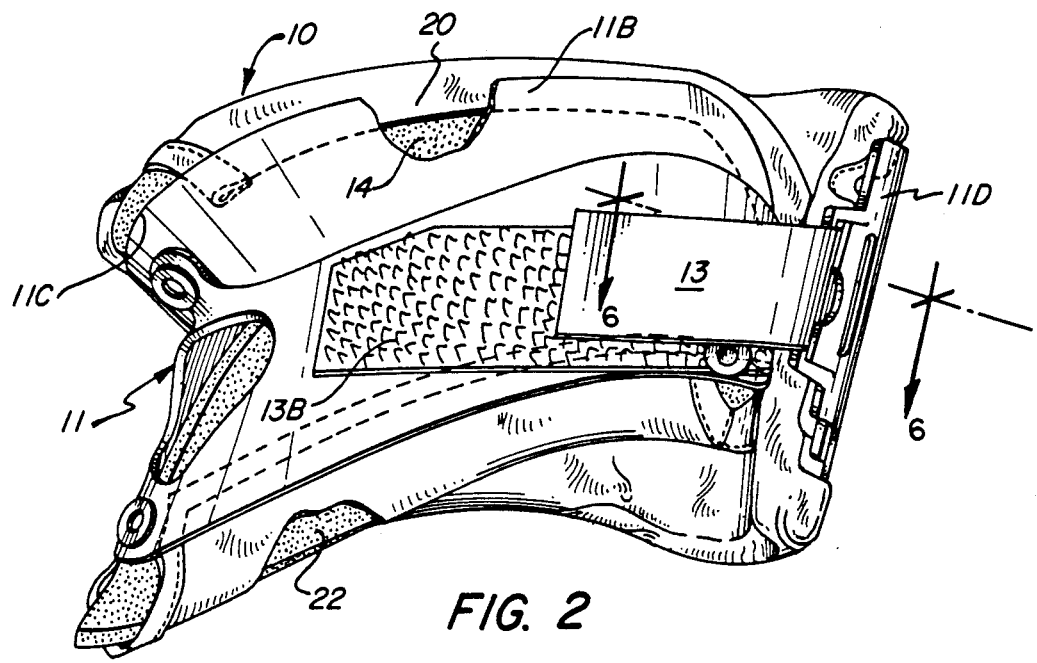
FIG. 2 is a perspective view of the surgical collar and liner of FIG. 1 in the assembled position.
Figure 4:
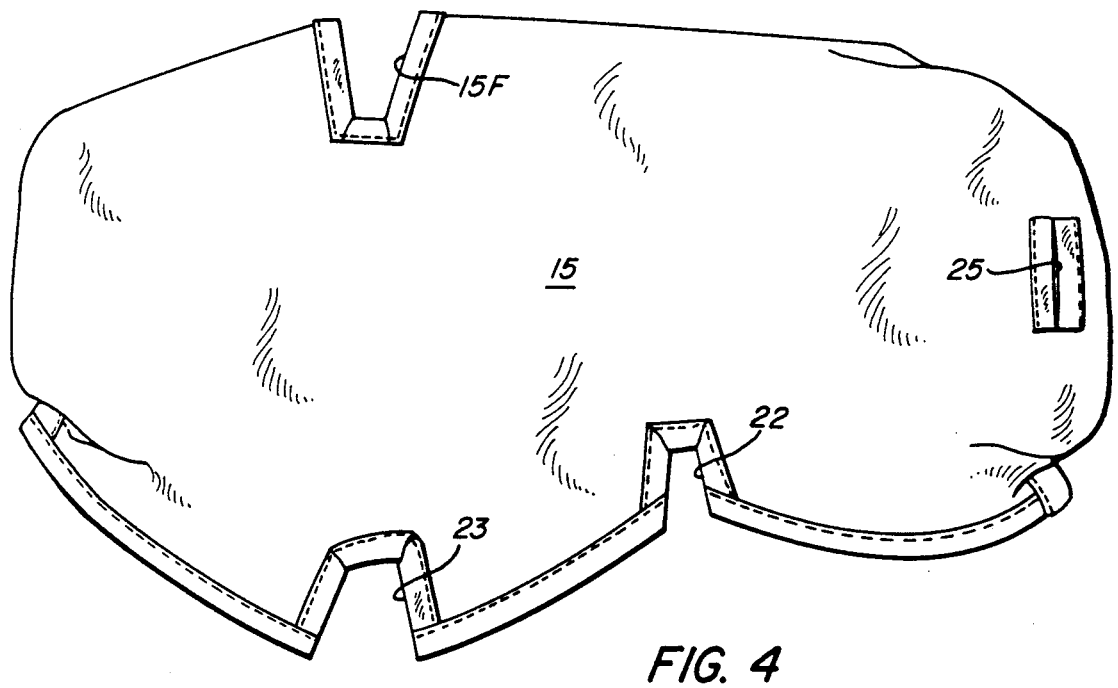
FIG. 4 is a plan view of FIG. 3 showing the inner or opposite surface of the liner which engages the neck of the wearer.

In assembling the liner 10 to the collar 11, the liner 10 is positioned on the interior of the collar 11 so that end 11E of the collar 11 is received within end pocket 18 of liner 10, and end 11D of the collar fitted into end pocket 19 of the liner. The fastening strap 13 is threaded through slit 25 and through an adjusting slot 27A formed in the end of the collar. See FIG. 1. The upper and lower marginal flap portions 20, 21 and 22A, 23A, 24A of the liner 10 respectively are then reversely folded about the upper and lower ends of the collar 11 and secured or folded between the plastic collar 11 and its foam pad 14 as best seen in FIG. 2. As indicated in FIGS. 2, 3 and 4, the liner blank is suitably notched at 15F and 23 to conform the liner 10 to the front curvature of the collar at the upper and lower front end thereof in the operative assembled position.

From the foregoing, it will be apparent that the liner 10 being formed of an absorbent material will readily absorb any perspiration, thereby rendering the collar more comfortable over an extended period of time. Also, by the use of the liner, the harsh feel of the plastic collar against the skin of the patient is avoided. As the liner is readily detachable and washable, the same can be readily washed and cleaned at frequent intervals, thereby avoiding the unpleasant gym odor of perspiration and/or rash which will otherwise occur during the wearing of the conventional collars.

Figure 7:
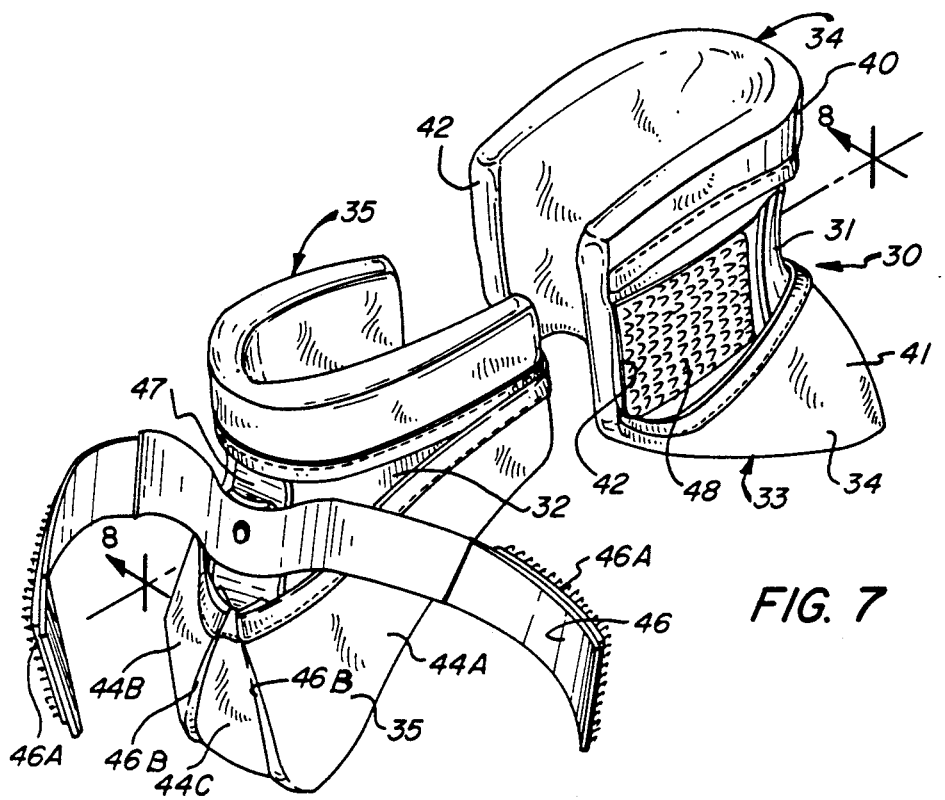
FIG. 7 illustrates a perspective view of a modified form of the invention.
Figure 8:
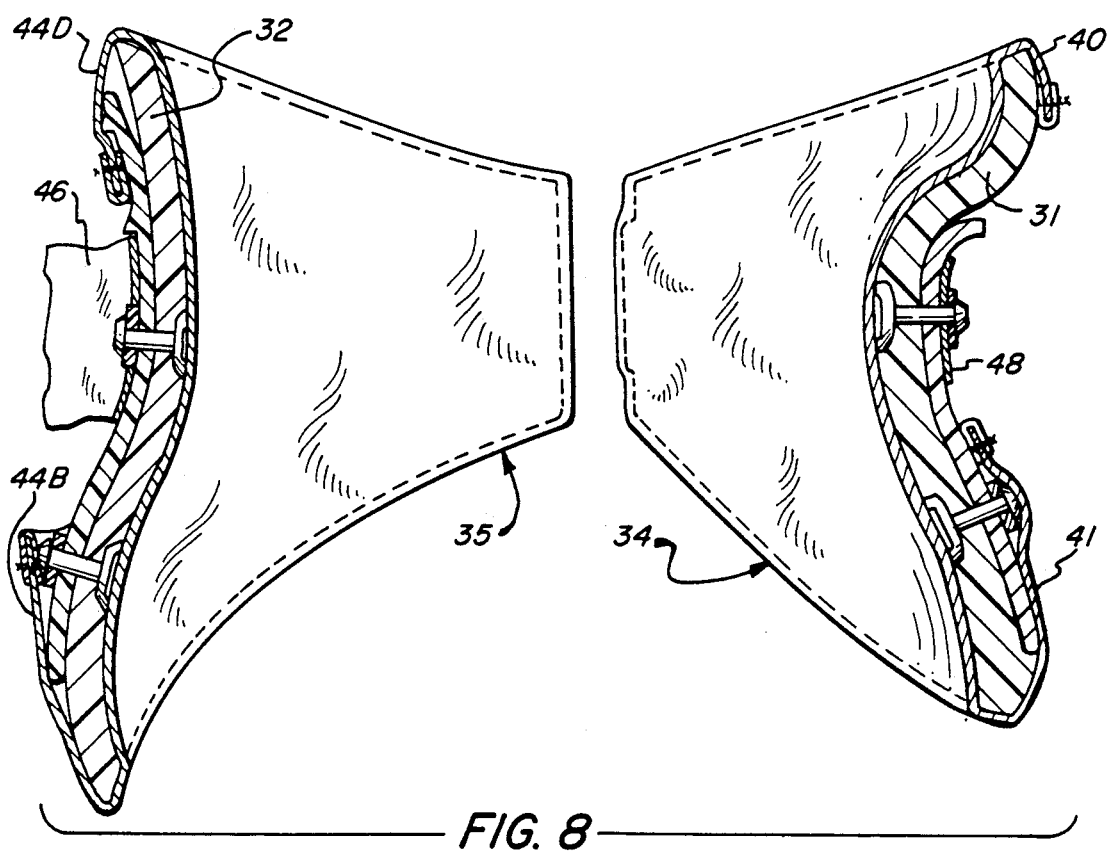
FIG. 8 is a sectional view taken along line 8-8 on FIG. 7.

FIGS. 7 and 8 illustrate a modified form of the invention. In this embodiment, the invention is applied to a surgical collar 30 comprising a pair of half sections 31 and 32 which define the front and back sections of the collar. In the illustrated embodiment, the front and back collar sections comprise a molded plastic foam section. Such collars are readily available. However, because of the inherent nature of a plastic foam and the inability of such material to absorb perspiration, such collars can become very uncomfortable when worn for an extended period of time. Thus, to obviate this problem, a liner is provided as hereinbefore described.

Figure 9:
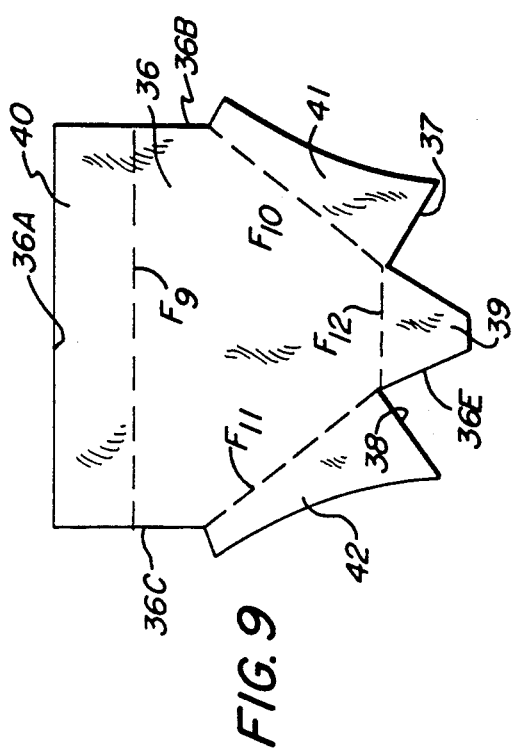
FIG. 9 is a plan view of a blank of sheet material from which the front half of the liner is made.
Figure 9A:
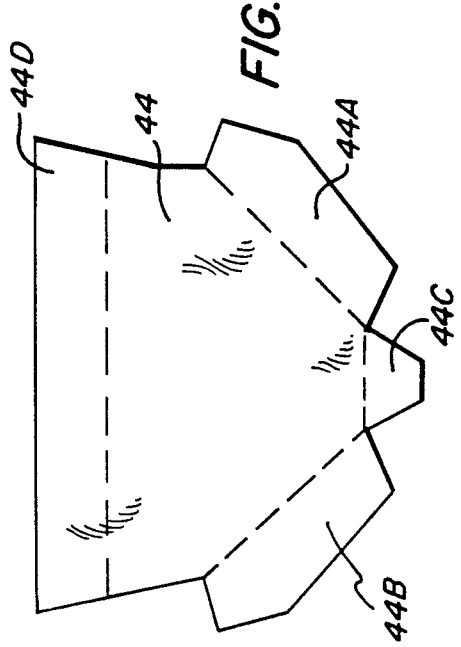
FIG. 9A is a plan view of a blank of sheet material from which the back half of the liner is made.
Figure 6:
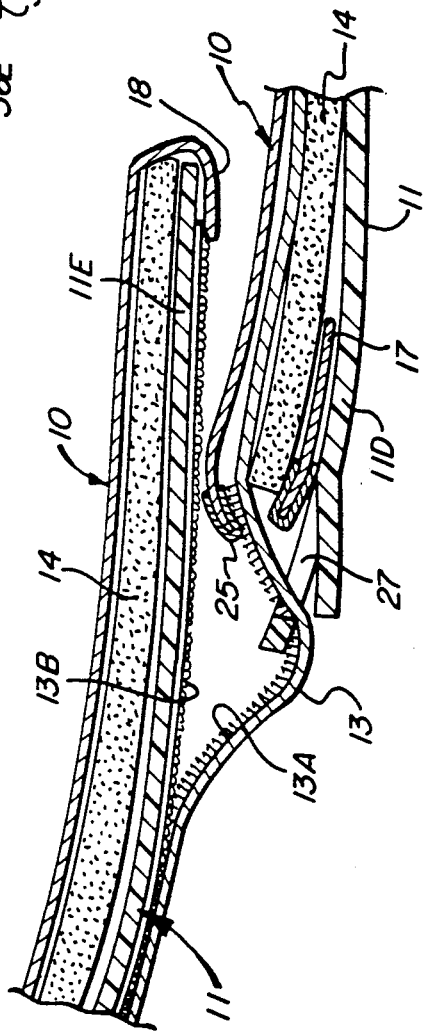
FIG. 6 is a sectional view taken along line 6-6 on FIG. 2.

In this form, the liner 33 comprises a two-part liner, a front portion 34 and a rear portion 35. Each portion 34 and 35 is formed of a blank of soft absorbent material, e.g., terrycloth. FIGS. 9 and 9A illustrate the general pattern for forming the front liner portion and rear liner portion 34 and 35 respectively.

Referring to FIG. 9, the pattern for forming the front liner portion 34 is substantially as shown. It comprises a blank 36 having a top edge 36A, similarly shaped side edges 36B and 36C and a bottom edge 36E having opposed V-shaped notches formed therein as indicated at 37 and 38 defining a center flap 39. Parallel to the top edge 36A is a foldline $F_9$ to define a top flap 40. Foldlines $F_{10}$ and $F_{11}$ define side flaps 41 and 42, and foldline $F_{12}$ defines the bottom flap 39.

To assemble the front pattern blank 36 to define the front liner portion 34, the side flaps 41 and 42 are reversely folded about their respective foldlines $F_{10}$ and $F_{11}$ as is the bottom flap 39, and the respective contiguous edges of the respective flaps are sewn together to form a pocket for receiving the bottom edge of the front collar section 31 as shown in FIG. 7. The upper marginal portion 40 is similarly reversely folded about the foldline $F_9$ to define an upper pocket for receiving the upper edge of the front collar section 31 as shown in FIG. 7. If desired, after the marginal flaps 40, 41, 42 and 39 have been folded and sewn, the opposed ends formed at 36B and 36C may be reversely folded to define end pockets as indicated at 42 to receive the end of the front collar section 31. With the blank 36 so formed, it will be noted that the front collar section 34 can be readily fitted to the liner section 34 so that the surface of the liner is against the skin of the wearer and the collar section 31 snuggly fitted to the liner section 34.

The blank 44 defining the rear liner section 35 is similarly shaped and similarly formed to the liner section 34. As seen in FIG. 7, the rear liner section 35, when formed like the front blank 44 as hereinbefore described, is similarly fitted to the rear or back collar section 32. FIG. 7 illustrates the sewn seam 46B, 46B by which the side marginal flaps 44A, 44B are secured to the bottom flap 44C in the assembled position of blank 44. The top marginal flap 44D is reversely folded to define the top pocket for receiving the upper edge of the rear collar section 32, as hereinbefore described with respect to pattern 36.

As noted in FIG. 7, the two half sections 31 and 32 of the collar with their respective liners can be readily applied to the neck of a patient and secured by hook and loop material fastening strap 46. As shown, the strap 46 is secured at an intermediate point 47 to the back of the rear collar section 32. The opposed ends of the strap are provided with the looped end of a hook and loop material 46A, 46A. The front section of the collar is provided on opposite sides thereof the complementary hook portion 48 of the hook and loop material fastener. Thus, with the liner sections 34 and 35 fitted to the respective half sections 31 and 32 of the collar, the respective sections can be readily applied to the patient and secured by mating the respective ends 46A of the strap to pad 48 of the front collar sections.

From the foregoing, it will be apparent that a readily simply constructed absorbent liner can be detachably connected to the conventionally known collars and thereby render the wearing of such collars more comfortable to the patient, and also avoiding the unpleasant odor associated with the wearing of such collars over an extended period of time due to perspiration.

While the invention has been described with respect to several embodiments thereof, it will be appreciated that variations and modifications may be made without departing from the spirit or scope of the invention.

What is claimed is:

1. A surgical collar and liner therefor, said collar and further including aperture means formed in said blank adapted to receive a portion of said collar having an upper longitudinal edge forming a chin rest, and opposed ends, and
    said liner comprising a flat blank of soft pliable absorbent material capable of being washed, adapted to cover the interior surface of said collar,
    said blank having opposed longitudinal extending marginal portions and opposed end portions,
    said opposed end portions of said blank being reversely folded to form an end pocket thereat between said opposed marginal portions,
    said end pockets being adapted to receive the opposed ends of said collar,
    said longitudinally extending marginal portions extending beyond the upper longitudinal edge and lower longitudinal circumscribing edge of said collar,
    said marginal portions being adapted to e outwardly and reversely folded over the longitudinal edge of said collar whereby said liner covers the interior surface of said collar and is releaseably secured to said collar solely by said marginal portions, said end pockets, and said aperture means.

2. The surgical collar and liner as defined in claim 1, wherein said marginal portions including notched out portions intermediate the ends thereof,
    said notched out portions being positioned to accommodate said chin rest and permitting said marginal portion to be reversely folded about the respective longitudinal edges of said collar.

3. A surgical collar and liner therefor as defined in claim 2 wherein said lower marginal portions having a notched portion disposed opposite said first mentioned notched portion allowing said lower marginal portion to be reversely folded about the lower peripheral edge of said collar in the operable position thereof.

4. A surgical collar and liner therefor,
    said surgical collar comprising a body portion adapted to circumscribe the neck of the wearer,
    said body having opposed end portions, and upper and lower longitudinally ending edge portions,
    said upper edge portion forming a chin rest at the front end of said collar and further including aperture means formed in said blank adapted to receive said fastening strap,
    and a fastening strap for securing the ends of the collar about a wearer's neck,
    a liner for covering the interior surface of said collar, said liner comprising a flat blank of soft pliable material sized to circumscribe and cover the inner surface of said collar,
    said blank having opposed end portions, and
    longitudinally extending marginal portions extending between said end portions of said blank,
    said end portions being reversely folded to define an end pocket for receiving an end portion of said collar,
    and said marginal portions being notched to allow said marginal portions to be reversely folded about the longitudinal edges of said collar in the operative position thereof whereby said liner covers the interior surface of said collar and is releaseably secured to said collar solely by said marginal portions, said end pockets and said aperture means.

5. A surgical collar and liner therefor as defined in claim 4 wherein said aperture means comprises a slit formed therein adjacent one end thereof whereby said fastening strap is adapted to be threaded through said slit for securing said collar and liner in the operative position.

6. A surgical collar and liner therefor as defined in claim 5 and including opposed notched portion disposed in said upper and lower marginal portions, said notched portion being positioned opposite the front end of said collar to facilitate the reverse folding of said marginal portions about the edges of said collar.

7. A liner for use with a surgical collar comprising a flat blank of soft pliable absorbent washable material,
    said blank having opposed end portions,
    said opposed end portions being outwardly and reversely folded to form an end pocket thereat,
    said end pockets being adapted to receive the opposed ends of a surgical collar,
    said blank having opposed longitudinally extending marginal portions adapted to be reversely folded along the longitudinal edges therof.
    said longitudinally extending marginal portions extending beyond the longitudinal edges of a surgical collar, and
    said longitudinally extending marginal portions being foldable outwardly and reversably about the longitudinal circumferential edges of the collar,
    at least one of said end pockets having a slit formed therein adapted for providing a pass through for the collar securing means.

* * * * *